United States Patent
Matsumoto et al.

(10) Patent No.: US 8,641,012 B2
(45) Date of Patent: Feb. 4, 2014

(54) MEDICAL CONNECTOR

(75) Inventors: Kuniaki Matsumoto, Takatsuki (JP); Katsuhiro Hiejima, Yasu (JP); Ken Suzuki, Kusatsu (JP); Akihiko Ishizaki, Amagasaki (JP)

(73) Assignee: Nipro Corporation, Osaka (JP)

( * ) Notice: Subject to any disclaimer, the term of this patent is extended or adjusted under 35 U.S.C. 154(b) by 189 days.

(21) Appl. No.: 13/132,777

(22) PCT Filed: Dec. 24, 2009

(86) PCT No.: PCT/JP2009/007152
§ 371 (c)(1),
(2), (4) Date: Jun. 3, 2011

(87) PCT Pub. No.: WO2010/073643
PCT Pub. Date: Jul. 1, 2010

(65) Prior Publication Data
US 2011/0233435 A1   Sep. 29, 2011

(30) Foreign Application Priority Data

Dec. 26, 2008   (JP) .................................. 2008-331716

(51) Int. Cl.
| | |
|---|---|
| *F16K 11/087* | (2006.01) |
| *F16L 37/28* | (2006.01) |
| *F16K 25/00* | (2006.01) |
| *A61M 25/16* | (2006.01) |
| *A61M 25/18* | (2006.01) |
| *A61M 39/02* | (2006.01) |

(52) U.S. Cl.
USPC .................. 251/149.6; 137/625.41; 251/192; 604/539

(58) Field of Classification Search
USPC ........ 251/149, 149.6, 358, 149.1, 149.5, 192; 604/284, 533, 537, 593; 137/625.41
See application file for complete search history.

(56) References Cited

U.S. PATENT DOCUMENTS 3,354,508 A * 11/1967 Draben ......................... 425/449
5,033,476 A    7/1991 Kasai
(Continued)

FOREIGN PATENT DOCUMENTS

| JP | A-2-502976 | 9/1990 |
|---|---|---|
| JP | U-4-13135 | 2/1992 |

(Continued)

OTHER PUBLICATIONS

Written Opinion of the International Searching Authority dated Jan. 26, 2010 issued in International Patent Application No. PCT/JP2009/007152 (with translation).

(Continued)

*Primary Examiner* — John K Fristoe, Jr.
*Assistant Examiner* — Frederick D Soski
(74) *Attorney, Agent, or Firm* — Oliff & Berridge, PLC

(57) ABSTRACT

A medical connector of improved configuration. Annular grooves are formed in both inner and outer surfaces of an outer peripheral portion of an elastic valve element to form an annular constricted section. An outer peripheral side from the constricted section is made to serve as an annular fixation section. A valve receiving seat is formed at an inner peripheral edge of an aperture portion in a housing, and an annular ring is fixed to the aperture portion to sandwich and support the annular fixation section between the valve receiving seat and the annular ring. Engaging projections formed on mutually facing surfaces of the valve receiving seat and the annular ring are engaged with the annular grooves, and either the engaging projection and/or the engaging projection is divided in a circumferential direction to have a plurality of projection-divisions.

11 Claims, 9 Drawing Sheets

(56) References Cited

U.S. PATENT DOCUMENTS

| | | | |
|---|---|---|---|
| 5,279,571 A | 1/1994 | Larkin | |
| 5,400,500 A | 3/1995 | Behnke et al. | |
| 5,549,576 A | 8/1996 | Patterson et al. | |
| 6,033,476 A | 3/2000 | Masukawa et al. | |
| 6,453,940 B1 * | 9/2002 | Tipton et al. | 137/493.9 |
| 6,651,956 B2 * | 11/2003 | Miller | 251/149.1 |
| 7,232,428 B1 * | 6/2007 | Inukai et al. | 604/248 |
| 2002/0193752 A1 | 12/2002 | Lynn | |
| 2006/0054586 A1 | 3/2006 | Sudo et al. | |
| 2006/0184140 A1 | 8/2006 | Okiyama | |
| 2007/0112311 A1 | 5/2007 | Harding et al. | |
| 2008/0108956 A1 * | 5/2008 | Lynn et al. | 604/256 |
| 2008/0306469 A1 | 12/2008 | Masuda et al. | |

FOREIGN PATENT DOCUMENTS

| | | |
|---|---|---|
| JP | A-8-509889 | 10/1996 |
| JP | A-2002-35122 | 2/2002 |
| JP | A-2002-78775 | 3/2002 |
| JP | A-2004-237133 | 8/2004 |
| JP | A-2006-110333 | 4/2006 |
| JP | A-2006-158603 | 6/2006 |
| JP | A-2007-202754 | 8/2007 |
| JP | A-2008-29606 | 2/2008 |
| WO | WO 89/06553 | 7/1989 |
| WO | WO 91/07206 | 5/1991 |
| WO | WO 2006/103074 A1 | 10/2006 |

OTHER PUBLICATIONS

International Search Report mailed Feb. 9, 2010 issued in International Patent Application No. PCT/JP2009/007152 (with translation).

Nov. 8, 2013 Office Action issued in Japanese Patent Application No. 2010-543867 (with translation).

* cited by examiner

MEDICAL CONNECTOR

TECHNICAL FIELD

The present invention relates to a medical connector that makes it possible to connect a medical connecting tool (male connector) to an infusion solution route when performing coinjection of a drug solution to an infusion solution route or collection of a biological fluid, or the like.

BACKGROUND ART

On an infusion solution route for performing solution infusion or blood collection, etc., there is typically provided a medical connector that makes it possible to connect a male connector such as a luer tip of a syringe tip, etc., in order to perform coinjection of a drug solution or perform collection of a biological fluid using this infusion solution route. For example, a three way stopcock widely used as a medical connector makes it possible to do coinjection of a drug solution using the already formed infusion solution route by forming an infusion solution route of a drip infusion or the like using a pair of the three aperture parts, permitting a connection of a male connector to the remaining one aperture part.

As one type of known medical connectors, Patent Document 1 (JP-A-2-502976) and Patent Document 2 (JP-A-2004-237133) disclose the so-called split septum type, for example. A split septum type medical connector is equipped with a disk shaped valve element at the aperture part, and by pressing and opening the slit by directly inserting the tip part of the male connector in the valve element slit, it is possible to have communication between the infusion solution route and the interior of the male connector.

BACKGROUND ART DOCUMENTS

Patent Documents

Patent Document 1: JP-A-2-502976
Patent Document 2: JP-A-2004-237133

SUMMARY OF THE INVENTION

Problem the Invention Attempts to Solve

However, with the split septum type medical connector, the valve element is relatively compact and thin, and when inserting the male connector into the slit, sufficiently ensuring adherence strength that can prevent falling out of the valve element was difficult. In light of this, in the past, the adherence strength was increased by ensuring the valve element hold margin outward in the radial direction, but increasing the scale of the valve element outer diameter dimensions brought on an increased scale of the connector size. Also, increased scale of the connector size becomes a cause of handling problems and an increase in manufacturing costs.

Also, when using a medical connector of a specific constitution, there was also the problem of having to go through a dedicated connector or the like. Specifically, as a connection method to the medical connector, two types are widely used, the luer slip type consisting of only a luer tip, and the luer lock type which has the female screw part provided on the outside of the luer tip fixed to the male screw part formed on the connector aperture part. However, as described above, due to the larger scale of the connector size due to larger diameter of the disk shaped valve element of the conventional constitution, there was the problem that it was not possible to directly connect a male connector of the standard size luer lock type in accordance with the ANSI and ISO standards.

Here, the present invention was created with the circumstances described above as the background, and it is accordingly an object of the present invention to provide an improved medical connector that can make the connector aperture part even smaller in diameter while ensuring the adherence strength of the valve element.

Means for Solving the Problem

A principle feature of the present invention provide a medical connector including: a housing having a fluid flow path internally; and a valve element mounted on an aperture portion of the fluid flow path of the housing, for which an external flow path is connectable to the fluid flow path of the housing via the valve element, characterized in that the valve element comprises a disk shaped elastic valve element having: a slit in a center portion; an annular constricted section provided by forming annular grooves extending in a circumferential direction respectively at both inner and outer surfaces of an outer peripheral portion thereof; and an annular fixation section provided at an outer peripheral side that is located outside of the annular constricted section, a valve receiving seat is provided at an inner peripheral edge portion of the aperture portion of the fluid flow path of the housing, an annular ring is adhered to the aperture portion, and the annular fixation section of the elastic valve element is sandwiched and supported by the valve receiving seat and the annular ring, engaging projections are respectively formed projecting on facing surfaces of the valve receiving seat and the annular ring, the engaging projections engage with the annular grooves formed on both the inner and outer surfaces of the elastic valve element, and at least one of the valve receiving seat engaging projection and the annular ring engaging projection is divided in the circumferential direction to have a plurality of projecting forms.

Effect of the Invention

Operation and Effect of the Present Invention
With a medical connector of a constitution according to the present invention, at least one of a pair of engaging projections engaged with the elastic valve element has a plurality of projection-divisions divided in the circumferential direction. Owing to this arrangement, the stress applied to the engaging projection via the elastic valve body when inserting or removing the male connector can be focused by each projection-divisions compared to when the engaging projection is continuous along the entire circumference. As a result, it is possible to hold the elastic valve element more strongly. Therefore, it is possible to make the aperture portion even smaller in diameter while sufficiently ensuring the elastic valve element adherence strength even without forming a large hold margin outward in the radial direction as was done in the past. As a result, it is possible to realize a more compact medical connector, and to obtain increased ease of handling, reduced manufacturing costs and the like.

Since the connector aperture portion can be made smaller in diameter, it becomes possible to also make the aperture portion smaller in diameter to the degree that it is possible to internally insert it in the female screw portion of a standard luer lock connector. For instance, by forming a male screw at the outer peripheral surface of the connector aperture portion, it is possible to connect directly to either of the male connector types, whether the luer slip type or the luer lock type, without going through any special connector.

Other Modes and Effects of the Present Invention

The present invention having the constitutional characteristics described above, may be practicable with the following modes in combination as appropriate according to necessity.

In one preferred mode of the invention, the plurality of projection-divisions of the engaging projection is in contact with a bottom surface of the annular groove of the elastic valve element, while a gap is provided inside the annular groove for which the engaging projection is not in contact. This arrangement makes it possible to ensure an escape space for elastic deformation of the elastic valve element by the gap, and to more reliably maintain strong holding of the elastic valve element.

In another preferred mode of the invention, the valve receiving seat is constituted by an annular valve receiving seat projecting on and integrally formed with an inner peripheral surface of the aperture portion of the fluid flow path of the housing, and the engaging projection is integrally formed at an inner peripheral edge portion of the annular valve receiving seat so as to project outwardly toward the aperture portion. This arrangement makes it possible to ensure a hold margin of the elastic valve element in the thickness direction of the elastic valve element, and to make the diameter dimensions of the elastic valve element smaller.

In yet another preferred mode of the invention, the annular ring is fit into an aperture edge portion of the fluid flow path of the housing, and the aperture edge portion of the fluid flow path is adhered to the annular ring by means of swaging processing. Specifically, as disclosed in the aforementioned Patent Document 1, for example, with a constitution for which swaging processing is done on the aperture edge portion of the fluid flow path and the elastic valve element is directly supported, control of the deformed portion is difficult, and holding the elastic valve element with stability is difficult. In contrast to this, with this preferred mode, since the aperture edge portion of the fluid flow path is adhered to the annular ring, it is possible to make control of the deformation portion easier, and it is possible to perform fixing of the elastic valve element with more stability. Furthermore, with the constitution directly supporting the elastic valve element at the aperture edge portion, a level difference occurs between the elastic valve element edge surface and the housing edge surface, and there is the risk that the sterilization of the edge surface before using the connector will be insufficient. In contrast to this, with this constitution, it is possible to form the elastic valve element end surface and the housing end surface on substantially one surface, so further improvement in terms of sanitation is possible.

In yet another preferred mode of the invention, the aperture portion of the fluid flow path at the housing is formed by adhering a separate cylinder shaped port to a hollow housing body, the cylinder shaped port is of a stepped cylinder shape consisting of a large diameter cylinder portion and a small diameter cylinder portion, and the cylinder shaped port is adhered to the housing body at the large diameter cylinder portion while a male screw portion is formed on an outer peripheral surface of the small diameter cylinder portion so that a female screw portion of a luer lock connector is connectable to the small diameter cylinder portion. This arrangement makes it possible to easily form the aperture portion of the housing equipped with an elastic valve element. Then, since a male screw portion is formed on a cylinder shaped port that is a separate member from the housing body, forming of the male screw portion is easier.

Also, the medical connector of the present invention can be suitably realized as a three way stopcock. That is, in another preferred mode of the invention, three branch aperture parts are provided on the housing, and a flow path switching mechanism of a rotation operation type is provided for selectively allowing communication of each internal fluid flow path connected to the three branch aperture parts. When realizing the medical connector of the present invention as a three way stopcock, for example, the elastic valve element is mounted on one of the three branch aperture parts.

EMBODIMENTS FOR CARRYING OUT THE INVENTION

Figure 1:
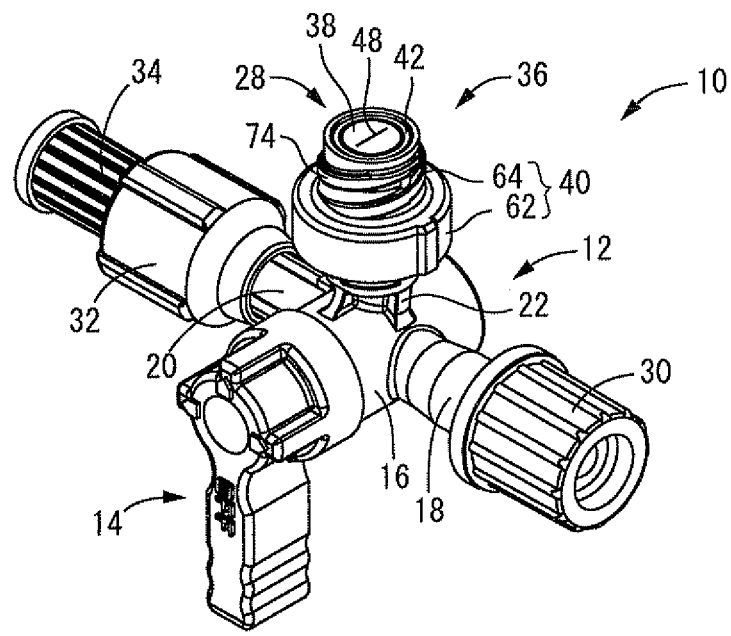
FIG. 1 is a perspective view of a medical connector as an embodiment of the present invention.

Following, we will give a detailed description of embodiments of the present invention while referring to the drawings.

Figure 2:
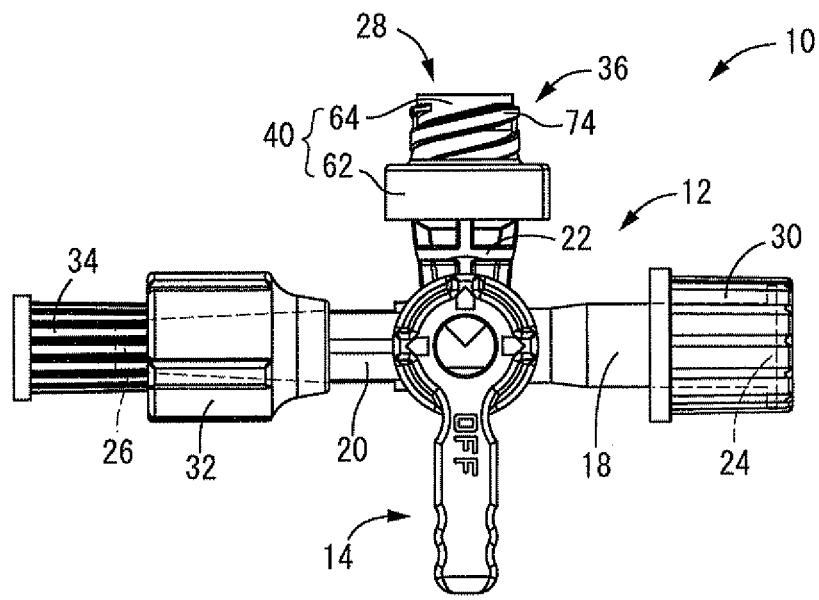
FIG. 2 is a front view of that medical connector.

First, FIG. 1 and FIG. 2 show a medical connector in the form of a three way stopcock 10 of the medical connector as an embodiment of the present invention. The three way stopcock 10 has a constitution for which a cock 14 is attached as a flow path switching mechanism to a holder 12 as the housing body. Note that the vertical direction in the description below means the vertical direction in FIG. 2 unless otherwise specified.

The holder 12 is a hollow constitution article formed integrally, equipped with a main unit portion 16 having a substantially round cylindrical shape, and first through third branch tubes 18, 20, and 22 projecting from the outer periphery of the main unit portion 16. These first through third branch tubes 18, 20, and 22 all have both ends parts of the axial direction in an open cylinder shape, with one axial direction end portion being connected to the main unit portion 16 and communicating with the internal space of the main unit portion 16, and the other end portion, as shown in model form by the dotted line in FIG. 2, set as the first through third branch aperture parts 24, 26, and 28 communicating with the external space of the holder 12. With this arrangement, the internal fluid flow paths connecting with the first through third branch aperture parts 24, 26, and 28 are respectively formed by the respective internal spaces of the first through third branch tubes 18, 20, and 22. Also, the first branch tube 18 and the second branch tube 20 are formed at a position facing opposite on the outer periphery of the main unit portion 16. Meanwhile, the third branch tube 22 is formed on the outer periphery of the main unit portion 16 with the first branch tube 18 and the second branch tube 20 at equal distance positions of 90 degrees.

On the three way stopcock 10 shown in FIG. 1 and FIG. 2, a female luer cap 30 for which a female screw is formed on the inner peripheral surface is detachably fixed by screwing in an externally inserted state to the first branch aperture part 24, on the second branch tube 20, a lock adapter 32 for which a female screw is formed on the inner peripheral surface is externally inserted engaged with the flange shaped portion (not illustrated) formed on the second branch tube 20 so that removal is impossible, and also, the male luer cap 34 is detachably attached in an externally inserted state to the second branch aperture part 26.

A cock 14 is liquid-tightly attached to be able to rotate on this main unit portion 16, and by doing a rotation operation of the cock 14, it is possible to selectively communicate with each internal fluid flow path connected to the first to third branch aperture parts 24, 26, and 28 formed by the internal space of the first to third branch tubes 18, 20, and 22.

Figure 3:
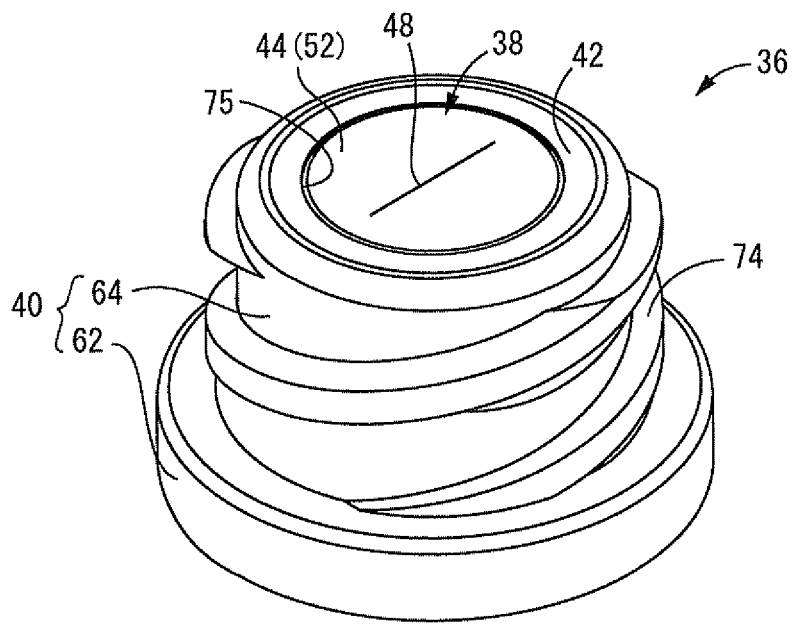
FIG. 3 is a perspective view of a coinjection port provided on that medical connector.
Figure 4:
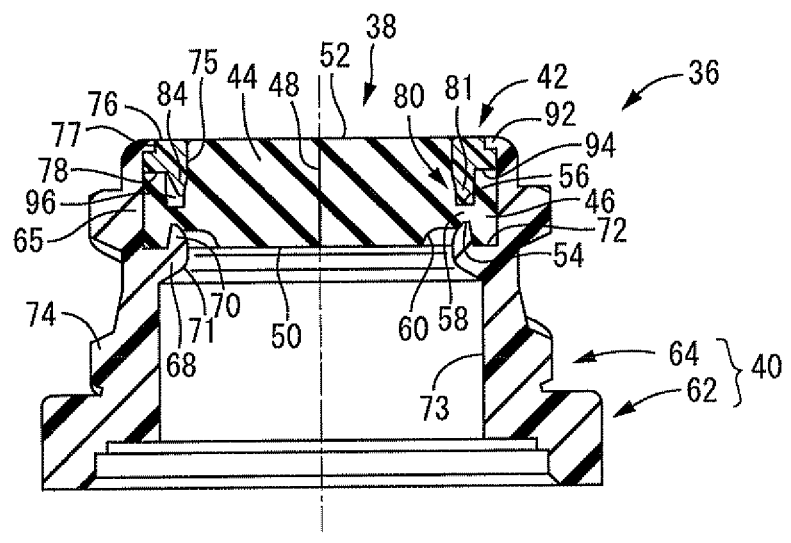
FIG. 4 is a cross section view of that coinjection port.
Figure 5:
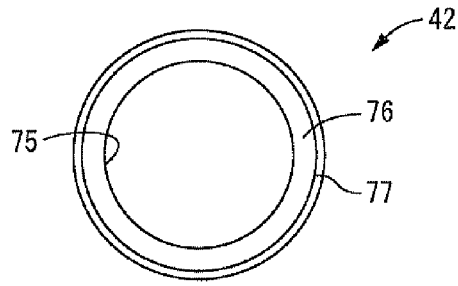
FIG. 5 is a top view of an annular ring constituting that coinjection port.
Figure 6:
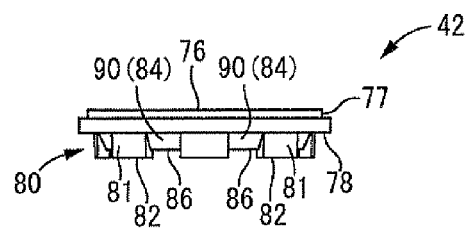
FIG. 6 is a side view of that annular ring.
Figure 7:
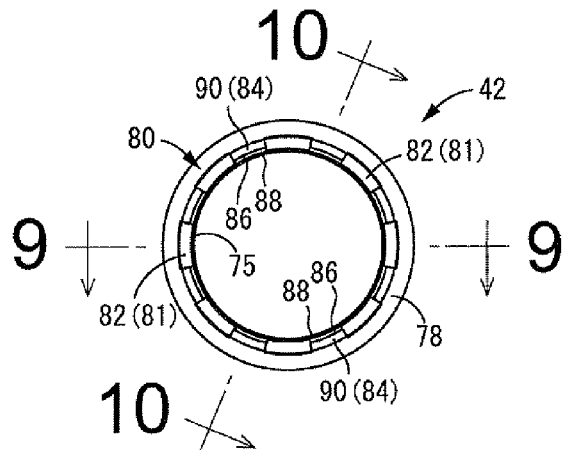
FIG. 7 is a bottom view of that annular ring.
Figure 8:
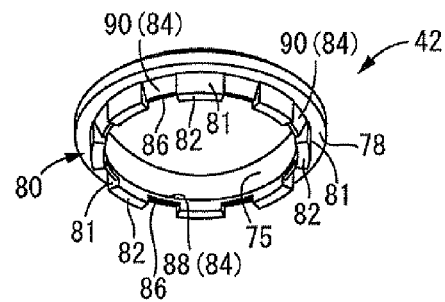
FIG. 8 is a perspective view of that annular ring.
Figure 9:
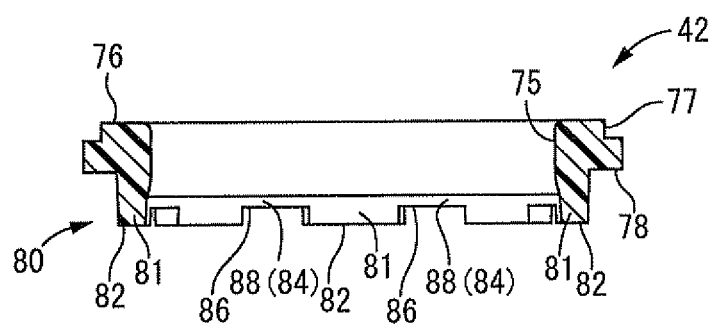
FIG. 9 is a cross sectional view taken along line 9-9 in FIG. 7.
Figure 10:
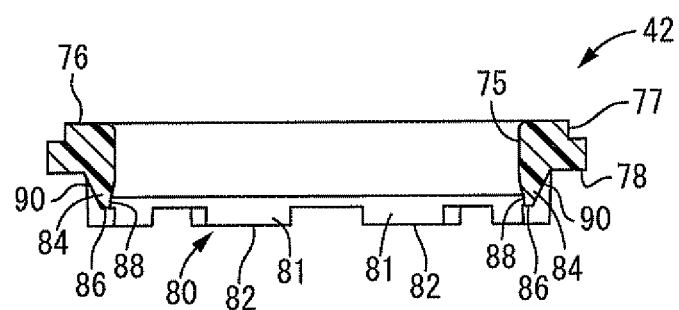
FIG. 10 is a cross sectional view taken along line 10-10 in FIG. 7.

Then, a coinjection port 36 is provided on the third branch aperture part 28. The coinjection port 36 is shown in FIG. 3 and FIG. 4. The coinjection port 36 is constituted including an valve element 38 as the elastic valve element having a disk shape, a cylinder shaped port 40, and an annular ring 42, and the valve element 38 is fixed by being sandwiched between these cylinder shaped port 40 and annular ring 42.

The valve element 38 is formed in a substantially circular disk form disk shape overall with a center portion 44 having a substantially circular disk shape and an annular fixation section 46 having a substantially round cylinder shape surrounding along the entire circumference of the outer periphery of the center portion 44 formed integrally. The valve element 38 is made of a material having elasticity, and considering airtightness and resealability, using a material selected from a synthetic rubber such as isoprene rubber, silicone rubber or the like, natural rubber, thermoplastic elastomer or the like, forming is done using press forming, mold forming or the like.

A slit 48 that pierces through in the thickness direction is formed on the center portion 44. As the shape of the slit 48, for example, a straight line shape or a cross shape is used, and with this embodiment, it is a straight line shape that passes through the center of the center portion 44, and extends in the radial direction of the center portion 44 to a level at which it does not reach the outer peripheral edge portion of the center portion 44. The slit 48 is formed with a sharp blade piercing in the formed valve element 38 thickness direction.

Meanwhile, the annular fixation section 46 has a substantially round cylinder shape extending continuously in the circumferential direction having a substantially constant square cross section shape, and this square cross section shape has a bigger axial direction dimension (vertical direction dimension in FIG. 4) than the wall thickness dimension (lateral direction dimension in FIG. 4) which is the radial direction dimension between the inner peripheral surface and the outer peripheral surface. At the inner surface 50 and the outer surface 52 of the valve element 38, while the inner surface of the annular fixation section 46 is fowled substantially on the same plane as the inner surface of the center portion 44, the outer surface of the annular fixation section 46 is formed slightly inward from the valve element 38 in the thickness direction of the valve element 38 (vertical direction in FIG. 4) compared to the outer surface of the center portion 44.

Also, at the outer peripheral portion for the inner surface 50 and the outer surface 52 of the valve element 38 are respectively formed extending continuously along the entire circumference annular grooves 54 and 56 having a concave cross section. The annular grooves 54 and 56 have mutually substantially equal radial direction width dimensions and are formed at mutually substantially equal positions in the radial direction of the valve element 38, and on the valve element 38 is formed by these annular grooves 54 and 56 an annular constricted section 58 with the thickness dimension made smaller. Therefore, with the valve element 38 of this embodiment, while the center portion 44 is formed at the inner periphery side of the constricted section 58, the annular fixation section 46 is formed at the outer periphery side of the constricted section 58, and these center portion 44 and annular fixation section 46 are formed integrally item connected by the constricted section 58. Also, the constricted section 58 is formed at a position slightly nearer the inner surface 50 in the thickness direction of the valve element 38, and the center portion 44 of the valve element 38 is made thicker on the outer surface 52 side of the constricted section 58.

Furthermore, a concave groove portion 60 extending continuously along the entire circumference is formed on the inside of the annular groove 54 at the inner surface 50. The concave groove portion 60 is formed with the edge portion of the radial direction outside equal to the edge portion of the radial direction inside of the annular groove 54, with a groove depth dimension slightly shallower than that of the annular groove 54. Also, the wall surface of the inner peripheral side of the concave groove portion 60 has a curved surface that rises smoothly from the bottom surface of the concave groove portion 60.

The diameter of the valve element 38 is preferably set within a range of 5.0 to 6.5 mm. As shown in FIG. 14 described later, this is because when the diameter of the valve element 38 is smaller than 5.0 mm, while insertion of the luer tip 106 of the standard luer lock connector 104 for which the outer diameter is unified to approximately 4.0 mm is difficult, when the diameter is larger than 6.5 mm, the outer diameter of the third branch aperture part 28 becomes large, and connection with the female screw portion 108 of the standard luer lock connector 104 is difficult.

Also, the thickness dimension of the valve element 38 is preferably set in a range within 1.0 to 3.0 mm. This is because when the thickness dimension of the valve element 38 is smaller than 1.0 mm, while there is the risk of a decrease in airtightness during insertion of the male connector, when the thickness dimension is larger than 3.0 mm, the male connector insertion resistance becomes large, and there is the risk of insertion becoming difficult.

This kind of valve element 38 is supported by the cylinder shaped port 40 formed separately from the holder 12. The cylinder shaped port 40 is a stepped round cylinder shape for which a large diameter cylinder portion 62 and a small diameter cylinder portion 64 are formed integrally. The inner diameter dimension of the small diameter cylinder portion 64 is made to be at least a size that can house the valve element 38 on the aperture portion 65 side (top side in FIG. 4), and so that there is stable manifestation of the resealed state of the slit 48 after removal of the male connector, preferably it should be substantially equal to the outer diameter valve element 38.

This cylinder shaped port 40 is preferably formed from a material having a strength that can reliably hold the valve element 38, and in specific terms, examples include thermoplastic resins such as polypropylene, polyethylene, polycarbonate, polystyrene, polyacetal and the like. Then, the cylinder shaped port 40 is formed from these materials using injection molding or the like.

Then, at the inner periphery edge portion of the aperture portion 65 at the small diameter cylinder portion 64, an annular valve receiving seat 68 is formed integrally, projecting in the radial direction inward. At the inner periphery edge portion of the valve receiving seat 68, an engaging projection 70 that projects outwardly in the opening direction (upward in FIG. 4) of the small diameter cylinder portion 64 is formed integrally. The engaging projection 70 is a peripheral wall shape that is continuous along the entire circumference having a constant projection height dimension.

Here, the portion that reaches from the inner peripheral surface of the engaging projection 70 to the inner peripheral surface of the valve receiving seat 68 is not closely adhered to the valve element 38 due to formation of the concave groove portion 60 on the inner surface 50 of the valve element 38, and there is exposure to the interior space of the cylinder shaped port 40 that forms the fluid flow path. In fact, this exposed surface corresponds to the concave groove portion 60 of the curved concave cross section surface formed on the valve element 38, and is used as a contacting inner peripheral surface 71 extending along the entire circumference in the circumferential direction with a constant cross section shape of a curved convex shape.

Note that with the small diameter cylinder portion 64, the peripheral wall inner surface positioned further inward in the axial direction than the site at which the engaging projection 70 is provided extending is used as a round cylindrical surface 73 extending linearly in the axial direction inward with a substantially constant inner diameter dimension.

Then, as described later, when the tip portion of a syringe or the like is inserted in the valve element 38, for the valve element 38 which is elastically deformed facing inward of the cylinder shaped port 40, the concave groove portion 60 is in contact with the contacting inner peripheral surface 71 of the engaging projection 70 and the valve receiving seat 68, and also, the inner surface 50 of the center portion 44 is made to contact the round cylindrical surface 73 of the small diameter cylinder portion 64. At that time, by having mutually corresponding shapes set at both surfaces that are in mutual contact, the respective contacting surfaces are made to have stable contact in a closely adhered state without having a gap.

Also, the projection height dimension of the engaging projection 70 is preferably equal to or slightly larger than the groove depth dimension from the inner surface at the annular fixation section 46 of the annular groove 54 formed at the inner surface 50 of the valve element 38. By doing this, the occurrence of a gap is prevented between the projection tip portion of the engaging projection 70 and the groove bottom portion of the annular groove 54 of the valve element 38.

Also, an annular fitting concave groove 72 extending along the entire circumference in the circumferential direction at the inner peripheral surface of the small diameter cylinder portion 64 is formed by the valve receiving seat 68 and the engaging projection 70. This fitting concave groove 72 opens towards the opening direction of the small diameter cylinder portion 64 of the cylinder shaped port 40. The depth dimension of this fitting concave groove 72 is the projection height dimension of the previously described engaging projection 70, and is equal to or slightly larger than the depth dimension of the annular groove 54 of the valve element 38. Also, the groove width dimension in the radial direction of the fitting concave groove 72 is the same or slightly smaller than the width dimension of the portion projecting in the axial direction inward direction (inner surface side) more than the constricted section 58 at the annular fixation section 46 of the valve element 38. By doing this, the annular fixation section 46 of the valve element 38 is in contact in a closely adhered state on the entire inner surface of the fitting concave groove 72, preventing a gap inside the fitting concave groove 72.

Also, on the outer peripheral surface of the small diameter cylinder portion 64 is formed a male screw portion 74 that screws together with the female screw portion 108 of the luer lock connector 104 described later. The male screw portion 74 is preferably a double threaded screw stipulated by ISO594 that can be connected with a female screw portion of a luer lock connector for which the screw peak diameter is set to 7.0±0.2 mm, and the screw valley diameter is set to 8.0±0.1 mm.

For the outer diameter dimensions of the cylinder shaped port 40, to make possible connection of a standard luer tip stipulated by ISO594, when not forming a male screw portion 74 like that of this embodiment, it is preferable to set the outer diameter of the small diameter cylinder portion 64 in a range from 6.0 to 7.0 mm, and when forming a male screw portion 74 like that of this embodiment, it is preferable to set the outer diameter of the small diameter cylinder portion 64 including the screw thread in a range from 7.2 to 8.0 mm.

Then, the annular ring 42 is adhered to the aperture portion 65 of the small diameter cylinder portion 64 at this cylinder shaped port 40. FIG. 5 through FIG. 10 show the annular ring 42. The annular ring 42 is a substantially round ring shape for which a through-hole 75 is formed at the center, and while its outer diameter dimension is substantially equal to the inner diameter dimension of the aperture portion 65 at the small diameter cylinder portion 64, the inner diameter dimension is substantially equal to the radial dimension of the center portion 44 at the valve element 38. Note that as the material of the annular ring 42, the same kind of thermoplastic resin as the cylinder shaped port 40 as described previously can be suitably used.

At the outer peripheral portion of an top edge surface 76 of this annular ring 42, an annular notch 77 is formed continuously along the entire circumference. Meanwhile, at the inner periphery portion of the bottom end surface 78 at the annular ring 42, an engaging projection 80 is formed integrally projecting downward. The engaging projection 80 specifically of this embodiment is a plurality of projection-divisions divided in the circumferential direction, constituted by a plurality (eight, with this embodiment) of projection-divisions 81 extending partially in the circumferential direction with a substantially square cross section shape. Also, specifically with this embodiment, the plurality of projection-divisions 81 are all formed having a substantially equal shape, and are formed at substantially equal gaps in the circumferential direction of the annular ring 42. In light of that, the radial direction width dimension of the projection end surface 82 of the projection-division 81 is substantially equal to the radial direction width dimension of the bottom surface of the annular groove 56 formed on the outer surface 52 of the valve element 38, and also, the projection height dimension of the projection-division 81 from the bottom end surface 78 of the annular ring 42 is substantially equal to the projection height dimension of the annular fixation section 46 from the constricted section 58 at the valve element 38.

Furthermore, a plurality (eight, with this embodiment) of auxiliary peripheral walls 84 projecting downward are formed integrally between the projection-divisions 81 on the circumference where the projection-divisions 81 are formed.

Here, the projection dimension of the auxiliary peripheral wall 84 is smaller than the projection-division 81, and also, the radial direction width dimension of the projecting end surface 86 of the auxiliary peripheral wall 84 is smaller than the radial direction width dimension of the projection end surface 82 of the projection-division 81. Also, while the inner peripheral surface 88 of the auxiliary peripheral wall 84 is a round cylindrical surface having constant diameter dimensions in the axial direction continuous with the inner peripheral surface of the projection-division 81, the outer peripheral surface 90 of the auxiliary peripheral wall 84 is a tapered surface slightly contracting as it goes downward.

The annular ring 42 is arranged at the outer peripheral portion except for the center portion 44 of the valve element 38, and so that there is no inhibition of the male connector connection operation, it is preferable that the inner diameter dimension of the through-hole 75 be set to 4.4 mm or greater. This is because if the inner diameter dimension of the through-hole 75 is smaller than 4.4 mm, when a standard luer lock connector stipulated by ISO594 is inserted, there is the risk that the luer tip and the annular ring 42 will be in contact and damage the luer tip, with loss of airtightness during connection.

After the valve element 38 has been inserted from the aperture portion 65 on the small diameter cylinder portion 64 side of the cylinder shaped port 40, the annular ring 42 is inserted from the aperture portion 65 on the small diameter cylinder portion 64 side, and the aperture edge portion 92 of the cylinder shaped port 40 is adhered to the annular ring 42. By doing this, the annular fixation section 46 of the valve element 38 is sandwiched by the valve receiving seat 68 of the cylinder shaped port 40 and the annular ring 42, and these cylinder shaped port 40, annular ring 42, and valve element 38 are mutually attached.

Figure 11:
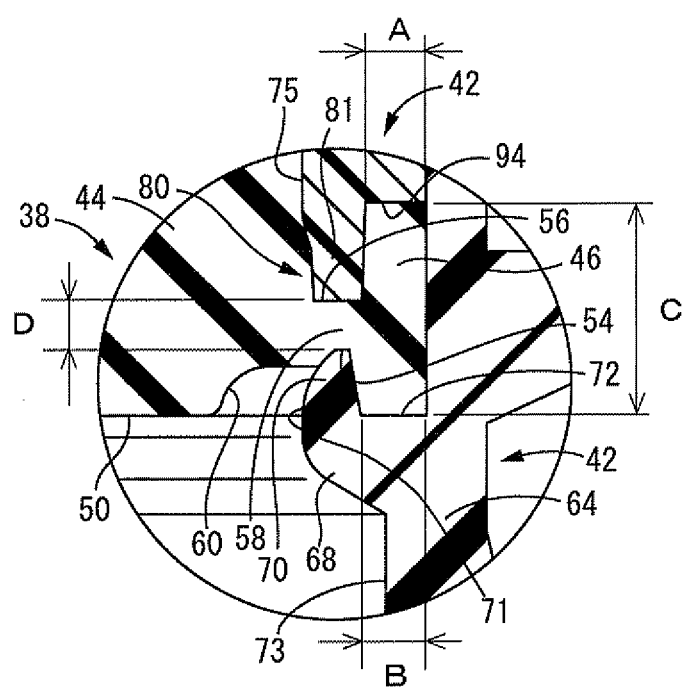
FIG. 11 is an enlarged cross section view of the major parts of the coinjection port shown in FIG. 3.

In this attached state, as shown in FIG. 11, the annular fixation section 46 at the valve element 38 is fit into the fitting concave groove 72, and also, the engaging projection 70 formed on the cylinder shaped port 40 is fit into the annular groove 54 formed on the inner surface 50 of the valve element 38. There, the projection end surface of the engaging projection 70 is in a contact state with the bottom surface of the annular groove 54.

Meanwhile, by mutually adhering the cylinder shaped port 40 and the annular ring 42, the fitting concave groove 94 that opens toward the valve receiving seat 68 is formed in the circumferential direction between the inner peripheral surface of the cylinder shaped port 40 and the projection-divisions 81. Then, the annular fixation section 46 at the valve element 38 is fit into this fitting concave groove 94, and also, the projection-divisions 81 formed on the annular ring 42 are fit into the annular groove 56 formed on the outer surface 52 of the valve element 38. There, the projection end surface of the projection-division 81 is in a contact state with the bottom surface of the annular groove 56. Meanwhile, at the annular groove 56, at the portion without formation of the projection-division 81 for which the auxiliary peripheral wall 84 is formed, a gap 96 (see FIG. 4) is formed between the bottom surface of the annular groove 56 and the annular ring 42.

Also, in the state with the annular ring 42 adhered to the cylinder shaped port 40, the projection-divisions 81 of the annular ring 42 and the engaging projection 70 of the cylinder shaped port 40 are positioned with a specified distance separated in the axial direction (vertical direction in FIG. 11) of the cylinder shaped port 40 on the surface facing opposite the annular ring 42 and the valve receiving seat 68 of the cylinder shaped port 40, and the constricted section 58 of the valve element 38 is extended out in the radial direction inward from the annular fixation section 46 passing between these projection-divisions 81 and engaging projection 70.

Specifically with this embodiment, the fitting concave groove 94 radial direction width dimension is set to A=approximately 0.4 mm, the fitting concave groove 72 radial direction width dimension is set to B=approximately 0.4 mm, the fitting concave groove 94 bottom surface and the fitting concave groove 72 bottom surface axial direction separation distance is set to C=approximately 1.3 mm, and the projection-division 81 and the engaging projection 70 axial direction separation distance is set to D=approximately 0.5 mm.

Furthermore, by the aperture edge portion 92 of the cylinder shaped port 40 being curved so as to enter into the interior of the annular notch 77 of the annular ring 42 and adhered to the annular ring 42, the top edge surface of the cylinder shaped port 40 and the top edge surface of the annular ring 42 are positioned on substantially the same plane. Together with that, the top edge surface of the annular ring 42 is positioned on substantially the same plane as the top edge surface of the valve element 38. By doing this, the top edge surface of the coinjection port 36 is formed as substantially a single plane.

Figure 12:
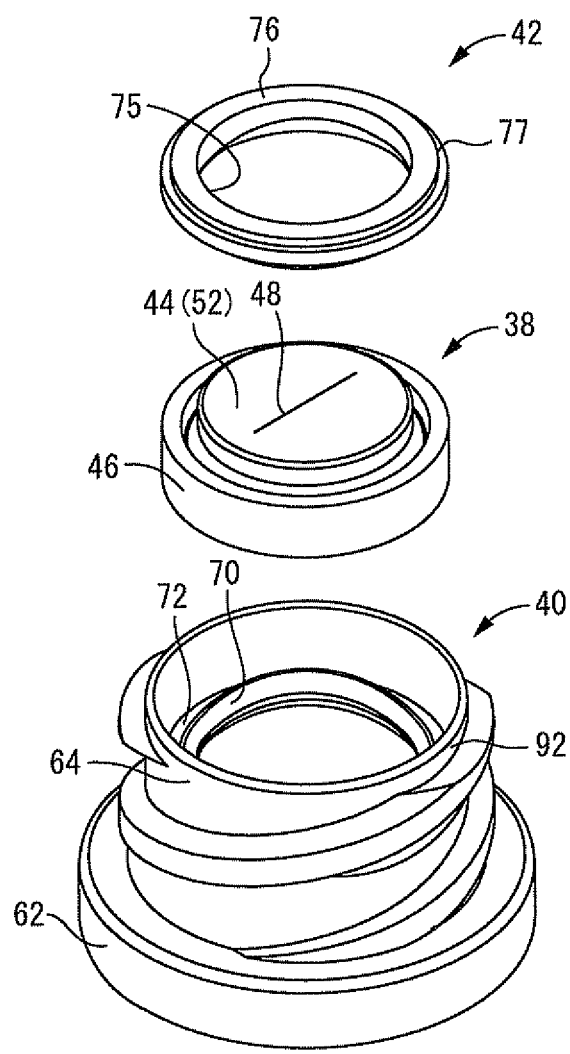
FIG. 12 is an exploded perspective view of that coinjection port.

The attachment of these valve element 38, cylinder shaped port 40, and annular ring 42 is performed advantageously by adhering the cylinder shaped port 40 and the annular ring 42 to each other using swaging processing. For example, first, as shown in FIG. 12, after the valve element 38 is fit into the cylinder shaped port 40, the annular ring 42 is fit into in the cylinder shaped port 40 from above the valve element 38. Note that at that stage, the aperture edge portion 92 of the cylinder shaped port 40 is not yet curved, and is a round cylinder shape extending in the axial direction. At the stage that this fitting is completed, the outer surface 52 of the valve element 38 and the top edge surface 76 of the annular ring 42 are positioned on substantially the same plane, and in relation to the top end surface of the cylinder shaped port 40, are positioned 0 to 0.2 mm above (see FIG. 13) or 0 to 0.1 mm below.

Figure 13:
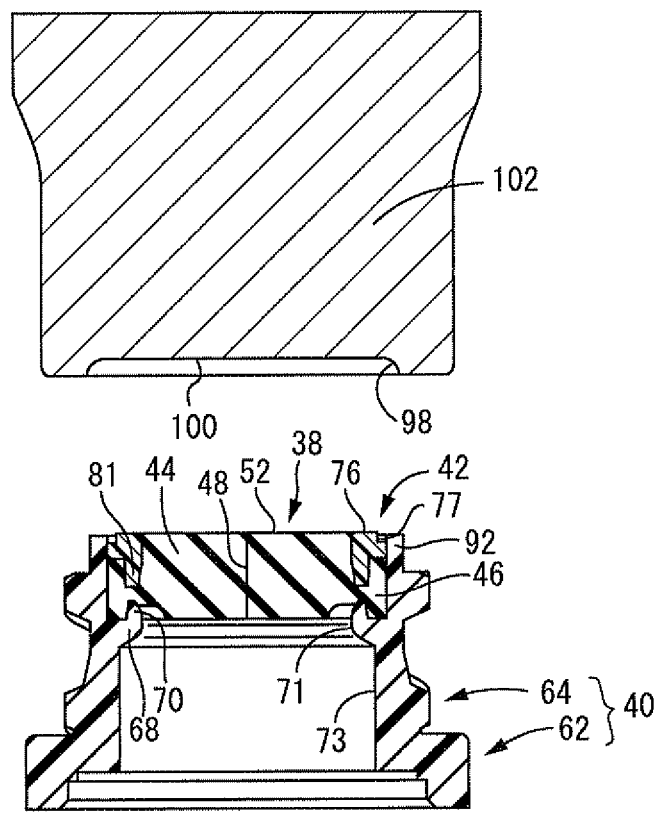
FIG. 13 is a cross section model diagram for describing the manufacturing method of that coinjection port.

Next, as shown in model form in FIG. 13, using a horn 102 having a round shaped concave portion 100 for which curved surface 98 is formed on the outer peripheral end portion, swaging processing is performed on the aperture edge portion 92 of the cylinder shaped port 40. By doing this, the top end portion of the cylinder shaped port 40 is deformed to the radial direction inside while being fused, and is joined with the outer peripheral edge portion of the annular ring 42. There, the aperture edge portion 92 of the fused cylinder shaped port 40 enters into the annular notch 77 formed on the annular ring 42, and the top end surface of the annular ring 42 is positioned on substantially the same plane projecting slightly in relation to the top end surface of the cylinder shaped port 40 and the top end surface of the valve element 38. Note that as a preferable processing condition for this kind of swaging processing, when using ultrasonic oscillation, it is preferable to set the ultrasonic oscillation frequency to approximately 20 to 40 Hz, to set the load at the time of oscillation to approximately 10 to 100 N, and to perform so that the sinking volume of the cylinder shaped port 40 which is the recess volume of the aperture edge portion 92 is 0.2 to 0.4 mm. Also, as the swaging processing, it is possible to use a means such as high frequency induction heating or the like instead of ultrasonic oscillation.

With a coinjection port 36 with this kind of constitution, the aperture portion of the third branch tube 22 at the holder 12 is covered by the large diameter cylinder portion 62 of the cylinder shaped port 40 and fixed. By doing this, with this embodiment, a housing is constituted for which a fluid flow path is formed inside containing the holder 12 and the cylinder shaped port 40, and the third branch aperture part 28 is constituted by the through-hole 75 of the annular ring 42 adhered to the aperture portion of the cylinder shaped port 40, and the valve element 38 is mounted on this third branch aperture part 28.

With the three way stopcock 10 with this kind of constitution, typically, by having the first branch aperture part 24 connected to the upstream side tube of the infusion solution route, and having the second branch aperture part 26 connected to the downstream side tube, portion of the infusion solution route is constituted by the first branch tube 18 and the second branch tube 20, and this is arranged on the infusion solution route.

Figure 14A:
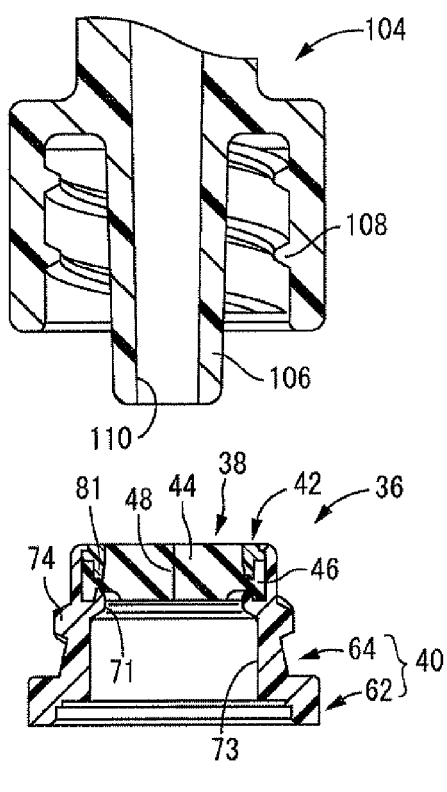
FIGS. 14A and 14B are cross section model diagrams for describing the connection method of that coinjection port.
Figure 14B:
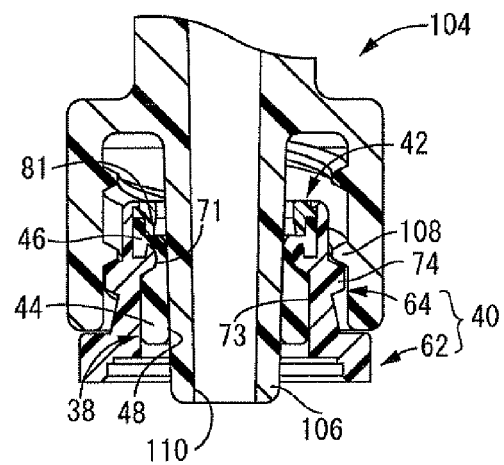

As shown in FIG. 14, for example a luer lock connector 104 is connected to the coinjection port 36 provided on the third branch aperture part 28. Note that FIG. 14A shows the state before connection of the luer lock connector 104, and FIG. 14B shows the state with the luer lock connector 104 connected. The luer lock connector 104 is an item widely known from the past having a standard size stipulated by ISO594, for example, and is equipped with a luer tip 106 forming an external flow path having a convergent round cylinder tapered shape, and a female screw portion 108 surrounding the outer periphery portion of the luer tip 106.

This luer tip 106 is pushed into the valve element 38 while screwing together the female screw portion 108 and the male screw portion 74 of the coinjection port 36. There, with the valve element 38, the annular fixation section 46 is engaged with the engaging projection 70 and the engaging projection 80. By doing this, the center portion 44 of the valve element 38 is pressed into the inward direction of the cylinder shaped port 40, and the slit 48 is pushed wider. As a result, as shown in FIG. 14B, the luer tip 106 pierces the valve element 38, and the tip aperture portion 110 is opened in the internal space of the cylinder shaped port 40, and the internal space of the for example syringe or the like connected to the luer tip 106 is in a state communicating with the internal fluid flow path of the third branch tube 22 through the fluid flow path inside the luer tip 106. Together with that, by the female screw portion 108 of the luer lock connector 104 being screwed together with the male screw portion 74 of the coinjection port 36, the inserted and passed through state of the luer tip 106 is reliably maintained. Note that with the coinjection port 36 according to this embodiment, in the connected state, the luer tip 106 is made to be offset from the internal peripheral surface of the cylinder shaped port 40 or the annular ring 42, and the luer tip 106 is made to be fixed by the elastic force of the valve element 38.

With this luer tip 106 in the inserted and passed through state, by operating the cock 14 and having the third branch tube 22 and the second branch tube 20 in a communicating state, it becomes possible for the drug solution filled inside the syringe to be coinjected in the infusion solution route. Then, after the coinjection is completed and the luer tip 106 is removed, by the elastic restoring force of the valve element 38, the center portion 44 returns to the round plate shape, and the slit 48 is blocked to be substantially airtight.

In FIGS. 14A and 14B, we showed as an example as the male connector a luer lock type connector having a female screw portion 108, but it is of course also possible to connect a connector of a so-called luer slip type which does not have a female screw portion 108, and is equipped only with a luer tip 106. Specifically with a luer slip type connector, the luer tip has the connected state maintained only with the elastic restoring force of the valve element 38. Also, in a case such as when only the luer slip type is the subject as the male connector, the cylinder shaped port 40 stepped shape and male screw portion 74 are not absolutely necessary.

With the three way stopcock 10 with this kind of constitution, of the engaging projections 70 and 80 that engage and hold the valve element 38, the engaging projection 80 provided on the annular ring 42 has a plurality of projection-divisions consisting of a plurality of projection-divisions 81. By doing this, the stress applied from the valve element 38 during insertion of the luer tip 106 can be concentrated on each projection-division 81 provided intermittently in the circumferential direction. As a result, it is possible to obtain a stable engaging holding force without making the hold margin larger, and it is possible to make the coinjection port 36 a smaller diameter. Then, by making the coinjection port 36 smaller in diameter, it is possible to improve the ease of handling and to lower the manufacturing cost, and the like. Furthermore, by making this coinjection port 36 smaller in diameter, it is possible to have external insertion of the female screw portion 108 of the luer lock connector to the coinjection port 36 and to screw them together.

Specifically, with the three way stopcock 10 in accordance with this embodiment, it has become possible to realize a smaller diameter coinjection port 36 while ensuring strong adherence strength of the valve element 38 with a very simple constitution, and with this smaller diameter, it becomes possible to connect either the standard luer lock type connector or the luer slip type connector without going through any special connector.

Furthermore, a gap 96 is formed in the portion where the projection-division 81 is not fit inside the annular groove 56, and by this gap 96, an escape area is formed during elastic deformation of the valve element 38. By doing this, it is possible to further decrease the risk of the valve element 38 coming out. Specifically with this embodiment, by having the outer peripheral surface 90 of the auxiliary peripheral wall 84 formed at the area where the projection-division 81 is not formed be a tapered surface, a larger gap 96 is secured.

In addition, the annular fixation section 46 is engaged with the engaging projections 70 and 80 projecting in the roughly axial direction of the cylinder shaped port 40 from both the inside and outside, and the contact area of the annular fixation section 46 and the cylinder shaped port 40 with the annular ring 42 is secured in the axial direction of the cylinder shaped port 40. By doing this, it is further possible to make the diameter smaller.

Then, by having the engaging projections 70 and 80 project in the axial direction of the cylinder shaped port 40, the constricted section 58 thickness dimension is smaller, and it becomes possible to more easily perform deformation of the center portion 44 during connection. Furthermore, by the concave groove portion 60 being formed on the inner surface 50 of the valve element 38, the interference with the valve receiving seat 68 and the engaging projection 70 during deformation when connecting is reduced, making deformation of the valve element 38 easier, and the risk of damage due to unreasonable stress being applied to the valve element 38 is also reduced. In addition, specifically with this embodiment, by having the inner peripheral surface of the valve receiving seat 68 and the engaging projection 70 be a smooth curved shape, it is possible to have the valve element 38 smoothly contact this inner peripheral surface, further reducing the risk of damage to the valve element 38.

Furthermore, with the luer tip 106 in a connected state, the luer tip 106 is held only by the valve element 38, and there is no contact with the cylinder shaped port 40 or the annular ring 42. By doing this, having something like contamination of chipped off resin can also be avoided, and there is further improvement in terms of sanitation.

In addition, with the coinfection port 36 with a constitution like that described above, the concave groove portion 60 of the valve element 38 and the contacting inner peripheral surface 71 of the engaging projection 70 and the valve receiving seat 68 to which the concave groove portion 60 contacts are formed having mutually corresponding curved concave cross section and curved convex cross section, so these have stable contact in a closely adhered state, and the occurrence of a gap between the contact surfaces is prevented. Because of that, it is possible to effectively avoid the entry and pooling of drug solution due to the occurrence of a gap.

In fact, after removal of the luer tip 106, in a state with the slit 48 closed by the valve element 38 being restored by elasticity, a recess with a sufficiently large aperture width is formed by the concave groove portion 60 formed on the valve element 38 on the surface of the contacting inner peripheral surface 71 of the engaging projection 70 and the valve receiving seat 68. Because of that, for example even if the drug solution enters in this concave groove portion 60, there is sufficient operation of a large gravity force compared to the stopping force on the concave groove portion 60 by the operation of surface tension, and pooling of drug solution in the concave groove portion 60 can be effectively avoided.

Also, the stress that occurs on the valve element 38 along with the curved deformation during insertion of the luer tip 106 is dispersed by the curved concave cross section set for the concave groove portion 60. In addition, the valve element 38, and the engaging projection 70 and valve receiving seat 68 that are in contact with the valve element 38 are formed having mutually corresponding curved concave cross section and curved convex cross section, so they exhibit a further dispersion effect of the stress and deformation on the valve element 38. By doing this, it is possible to reduce the decrease in durability due to the local operation of stress and deformation on the valve element 38. As a result, the plastic deformation of the valve element 38 is suppressed, and it is possible to effectively prevent new occurrence of a gap that comes with repetition of attachment and removal of the luer tip 106 in the valve element 38, and the problem of pooling of drug solution and the like due to that.

While one embodiment of the present invention has been described in detail, this is nothing more than an example, and the present invention is not limited to interpretation by the specific notations of that embodiment.

For example, with the aforementioned embodiment, the engaging projection 80 consisting of a plurality of projection-divisions 81 were provided only on the annular ring 42, but instead of or in addition to the annular ring 42, it is also possible to have the engaging projection 70 of the cylinder shaped port 40 be a plurality of projection-divisions. Also, the auxiliary peripheral wall 84 provided between the projection-divisions 81 is not absolutely necessary.

Also, the specific number or shape of the projection-division, the circumferential direction dimensions and the like can be set as appropriate considering the valve element size or the required adherence strength or the like, and this is not limited to the specific constitution like that of the aforementioned embodiment. Therefore, it is also possible to for example have mutually different circumferential direction dimensions for the plurality of projection-divisions, to provide unequal gaps in the circumferential direction or the like.

Also, with the aforementioned embodiment, the valve receiving seat 68 is formed on the cylinder shaped port 40, and the valve element 38 is supported by the cylinder shaped port 40 formed as a separate body from the holder 12, but it is also possible for example to form a valve receiving seat directly on the housing body, and with the aforementioned embodiment, it is also possible to form a valve receiving seat on the aperture portion of the third branch tube 22 for the holder 12.

The aforementioned embodiment illustrates one example of the medical connector equipped with a three way stopcock housing. However, as the housing of the present invention, it is possible to suitably apply all various housing shapes used for prior known medical connectors. For example, as shown in FIGS. 15A, 15B, and 15C, it is of course possible to apply the present invention to a coinjection plug 112, a coinjection tube 114, a drug bag 116 or the like.

Figure 15A:
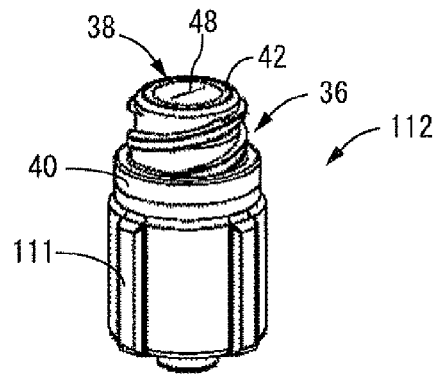
FIGS. 15A-15C are perspective views each showing a medical connector as another embodiment of the present invention, where 15A shows an example applied to a coinjection plug, 15B a coinjection tube, and 15C a drug bag.
Figure 15B:
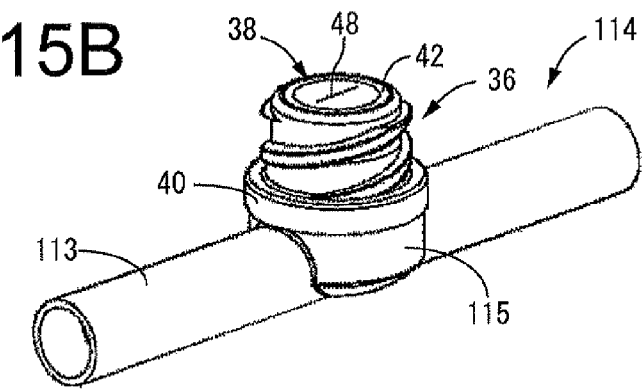
Figure 15C:
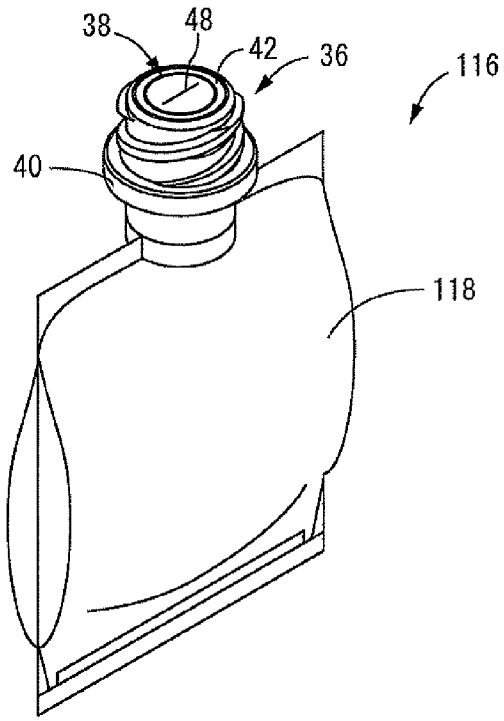

In more detail, with the coinjection plug 112 shown in FIG. 15A, one of the aperture portions of the cylindrical plug body 111 as the housing body is attached liquid-tightly to the cylinder shaped port 40 of the coinjection port 36 of the aforementioned embodiment. Specifically, instead of the three way stopcock housing of the aforementioned embodiment, the housing is formed by these cylinder shaped port 40 and plug body 111, and the coinjection plug 112 is constituted as the medical connector. Also, with the coinjection tube 114 shown in FIG. 15B, the cylindrical attachment portion 115 is provided opened upward in relation to the elongated infusion solution tube 113 so as to constitute the housing body, and the cylinder shaped port 40 of the coinjection port 36 of the aforementioned embodiment is attached liquid-tightly to the aperture portion of this attachment portion 115. The housing is formed by these cylinder shaped port 40, the infusion solution tube 113, and the attachment portion 115, and the coinjection tube 114 is constituted as the medical connector. Furthermore, with the drug bag 116 shown in FIG. 15C, by having the cylinder shaped port 40 of the coinjection port 36 stretch out to have a cylinder shape, this is connected with the bag body 118 as the housing body in which is sealed various types of drugs or normal saline solution or the like. The bag body 118 is constituted with a sheet material of a synthetic resin or the like on which aluminum is evaporated, and by having the aperture perimeter portion blocked by adhesion or the like and tightly sealed integrally with the coinjection port 36, the coinjection port 36 and the bag body 118 are liquid-tightly coupled and connected. The housing is formed by these cylinder shaped port 40 and the bag body 118, and the drug bag 116 is constituted as the medical connector.

In addition, though we will not list them individually, the present invention can be implemented in modes with the addition of various changes, modifications, and improvements, etc. based on the knowledge of a person skilled in the art, and it goes without saying that such embodiments, unless they stray from the spirit of the present invention, are all included in the scope of the present invention.

EXPLANATION OF CODES

10: three way stopcock, 12: holder, 24: first branch aperture part, 26: second branch aperture part, 28: third branch aperture part, 36: coinjection port, 38: valve element, 40: cylinder shaped port, 42: annular ring, 44: center portion, 46: annular fixation section, 48: slit, 54: annular groove, 56: annular groove, 58: constricted section, 68: annular valve receiving seat, 70: engaging projection, 80: engaging projection, 81: projection-divisions, 112: coinjection plug, 114: coinjection tube, 116: drug bag

The invention claimed is:

1. A medical connector comprising:
   a housing having a fluid flow path internally;
   a disk shaped elastic valve element mounted on an aperture portion of the fluid flow path of the housing, for which an external flow path is connectable to the fluid flow path of the housing via the valve element;
   the disk shaped elastic valve element having:
      a slit in a center portion;
      an annular constricted section provided by forming annular grooves extending in a circumferential direction respectively at both inner and outer surfaces of an outer peripheral portion thereof; and
      an annular fixation section provided at an outer peripheral side that is located outside of the annular constricted section;
   a valve receiving seat being provided at an inner peripheral edge portion of the aperture portion of the fluid flow path of the housing;
   an annular ring being adhered to the aperture portion, the annular fixation section of the elastic valve element being sandwiched and supported by the valve receiving seat and the annular ring; and
   engaging projections respectively formed projecting on facing surfaces of the valve receiving seat and the annular ring, wherein
      the engaging projections engage with the annular grooves formed on both the inner and outer surfaces of the elastic valve element,
      at least one of the valve receiving seat engaging projection and the annular ring engaging projection is divided in the circumferential direction to have a plurality of projection-divisions, and
      auxiliary peripheral walls are provided between the circumferentially adjacent projection-divisions with a projection dimension smaller than that of the projection-divisions, and both of the projection-divisions and auxiliary peripheral walls are placed within the annular groove.

2. The medical connector according to claim 1, wherein the plurality of projection-divisions of the engaging projection is in contact with a bottom surface of the annular groove of the elastic valve element, while a gap is provided inside the annular groove for which the engaging projection is not in contact.

3. The medical connector according to claim 1, wherein the valve receiving seat is constituted by an annular valve receiving seat projecting on and integrally formed with an inner peripheral surface of the aperture portion of the fluid flow path of the housing, and the engaging projection is integrally formed at an inner peripheral edge portion of the annular valve receiving seat so as to project outwardly toward the aperture portion.

4. The medical connector according to claim 1, wherein the annular ring is fit into an aperture edge portion of the fluid flow path of the housing, and the aperture edge portion of the fluid flow path is adhered to the annular ring by means of swaging processing.

5. The medical connector according to claim 1, wherein the aperture portion of the fluid flow path at the housing is formed by adhering a separate cylinder shaped port to a hollow housing body, the cylinder shaped port is of a stepped cylinder shape consisting of a large diameter cylinder portion and a small diameter cylinder portion, and the cylinder shaped port is adhered to the housing body at the large diameter cylinder portion while a male screw portion is formed on an outer peripheral surface of the small diameter cylinder portion so that a female screw portion of a luer lock connector is connectable to the small diameter cylinder portion.

6. The medical connector according to claim 1, wherein three branch aperture parts are provided on the housing, and a flow path switching mechanism of a rotation operation type is provided for selectively allowing communication of each internal fluid flow path connected to the three branch aperture parts so as to provide a three way stopcock, while the elastic valve element is mounted on one of the three branch aperture parts.

7. The medical connector according to claim 1, wherein the housing includes a plug body so as to provide a coinjection plug.

8. The medical connector according to claim 1, wherein the housing includes an infusion solution tube so as to provide a coinjection tube.

9. The medical connector according to claim 1, wherein the housing includes a bag body so as to provide a drug bag.

10. The medical connector according to claim 1, wherein each of the auxiliary peripheral walls has an outer peripheral surface being tapered slightly radially inwardly in a direction towards a projecting end thereof.

11. The medical connector according to claim 1, wherein inner peripheral surfaces of the auxiliary peripheral walls provide a round cylindrical surface having a constant diameter dimension in an axial direction continuous with inner peripheral surfaces of the projection-divisions.

* * * * *